(12) United States Patent
Tsai et al.

(10) Patent No.: US 12,721,656 B2
(45) Date of Patent: Sep. 1, 2026

(54) ASSEMBLEABLE ARTIFICIAL BONE PLATE AND ARTIFICIAL BONE PLATE UNIT

(71) Applicant: Ji Yan Biomedical Co., Ltd, Taipei City (TW)

(72) Inventors: Tung-Kuo Tsai, New Taipei City (TW); Keng-Liang Ou, Kaohsiung City (TW); Yung-Kang Shen, New Taipei City (TW); Yin-Chung Huang, New Taipei City (TW); Kuo-Sheng Hung, New Taipei City (TW); Yu-Sin Ou, Kaohsiung City (TW)

(73) Assignee: Ji Yan Biomedical Co., Ltd., Taipei City (TW)

( * ) Notice: Subject to any disclaimer, the term of this patent is extended or adjusted under 35 U.S.C. 154(b) by 787 days.

(21) Appl. No.: 17/970,774

(22) Filed: Oct. 21, 2022

(65) Prior Publication Data

US 2024/0130762 A1 Apr. 25, 2024
US 2024/0225701 A9 Jul. 11, 2024

(51) Int. Cl.
*A61F 2/00* (2006.01)
*A61B 17/56* (2006.01)
(Continued)

(52) U.S. Cl.
CPC .......... *A61B 17/688* (2013.01); *A61B 17/808* (2013.01); *A61F 2/2875* (2013.01); *A61B 17/8061* (2013.01); *A61F 2310/00023* (2013.01)

(58) Field of Classification Search
None
See application file for complete search history.

(56) References Cited

U.S. PATENT DOCUMENTS 5,368,704 A * 11/1994 Madou ................ A61M 31/002 204/278
5,797,898 A * 8/1998 Santini, Jr. ................ C25F 7/00 604/890.1

(Continued)

FOREIGN PATENT DOCUMENTS

AU 2002355020 A1 * 6/2003 ............. A61L 27/56
CN 208388806 U 1/2019

(Continued)

*Primary Examiner* — Ann Hu
(74) *Attorney, Agent, or Firm* — Best & Flanagan LLP

(57) ABSTRACT

An artificial bone plate unit and an assembleable artificial bone plate are provided. The artificial bone plate unit includes a plate body, multiple connecting pins, connecting holes, drug cavities, and drug-releasing openings. The plate body has two main surfaces and a peripheral surface connected between the two main surfaces. The connecting pins and the connecting holes are formed on the plate body and arranged along the peripheral surface on the plate body. The connecting holes correspond in shape to the connecting pins. The drug cavities are formed in the artificial bone plate unit and are connected to the drug-releasing openings. The artificial bone plate units are connected using the connecting pins and the connecting holes to form the assembleable artificial bone plate. The assembleable artificial bone plate can be bent into the shape of a defect area of the skull, which saves material and time.

17 Claims, 18 Drawing Sheets

(51) Int. Cl.

| | |
|---|---|
| ***A61B 17/68*** | (2006.01) |
| ***A61B 17/80*** | (2006.01) |
| ***A61F 2/28*** | (2006.01) |
| ***A61K 35/32*** | (2015.01) |
| ***A61K 38/18*** | (2006.01) |
| ***A61L 27/02*** | (2006.01) |
| ***A61L 27/54*** | (2006.01) |

(56) References Cited

U.S. PATENT DOCUMENTS

| | | | | |
|---|---|---|---|---|
| 6,558,422 | B1 * | 5/2003 | Baker | A61F 2/0077 623/1.42 |
| 8,795,377 | B2 * | 8/2014 | Engqvist | A61L 31/026 623/17.17 |
| 9,623,151 | B2 * | 4/2017 | Jin | A61K 31/7088 |
| 11,045,321 | B2 * | 6/2021 | Stübinger | A61F 2/28 |
| 11,426,266 | B2 * | 8/2022 | Mathisen | A61F 2/12 |
| 2003/0039676 | A1 * | 2/2003 | Boyce | A61F 2/32 623/16.11 |
| 2005/0015088 | A1 * | 1/2005 | Ringeisen | A61L 31/146 606/908 |
| 2005/0031665 | A1 * | 2/2005 | Watson | A61B 17/8615 606/218 |
| 2005/0273165 | A1 * | 12/2005 | Griffiths | A61C 8/0006 606/70 |
| 2005/0278027 | A1 * | 12/2005 | Hyde | A61F 2/442 623/17.11 |
| 2007/0088442 | A1 * | 4/2007 | Cima | A61B 5/4528 600/431 |
| 2008/0097445 | A1 * | 4/2008 | Weinstein | A61B 17/8023 606/151 |
| 2011/0159070 | A1 * | 6/2011 | Jin | A61K 9/127 228/174 |
| 2014/0195004 | A9 | 7/2014 | Engqvist et al. | |
| 2019/0380836 | A1 | 12/2019 | Stubinger et al. | |
| 2020/0246148 | A1 | 8/2020 | Gelse et al. | |
| 2020/0405353 | A1 * | 12/2020 | Ou | A61B 17/808 |
| 2022/0354553 | A1 | 11/2022 | Kamath | |

FOREIGN PATENT DOCUMENTS

| | | | | |
|---|---|---|---|---|
| CN | 208551999 | U | 3/2019 | |
| CN | 111821070 | A * | 10/2020 | A61F 2/2875 |
| CN | 115153920 | A * | 10/2022 | A61C 19/063 |
| JP | 2001258913 | A * | 9/2001 | A61F 2/28 |
| JP | 2008114029 | A | 5/2008 | |
| TW | M639236 | U | 4/2023 | |
| WO | WO-2010003062 | A2 * | 1/2010 | A61P 43/00 |
| WO | WO-2011010463 | A1 * | 1/2011 | A61F 2/28 |
| WO | 2017/039762 | A1 | 3/2017 | |

* cited by examiner

ASSEMBLEABLE ARTIFICIAL BONE PLATE AND ARTIFICIAL BONE PLATE UNIT

1. FIELD OF THE INVENTION

The present invention relates to a medical implant, especially to an assembleable artificial bone plate and an artificial bone plate unit that can be used for cranioplasty, i.e., surgical repair of a bone defect in the skull.

2. DESCRIPTION OF THE PRIOR ARTS

After removal of a large area of a skull of a patient due to trauma or operation, cranioplasty needs to be carried out to repair the defect area in the skull using an artificial bone plate to cover the defect area of the skull. The artificial bone plate provides proper protection for the vulnerable brain tissue and prevents sequelae.

A conventional artificial bone plate used in cranioplasty is cut by machining from a chunk of material; to be precise, a chunk of metal or polymer is cut into the shape of the removed bone of the skull, and then the machined artificial bone plate is fixed to the skull by surgery.

However, the surface of the skull is curved, and therefore a great amount of material needs to be removed during the machining process, which causes a waste of material and time.

To overcome the shortcomings, the present invention provides an assembleable artificial bone plate and an artificial bone plate unit to mitigate or obviate the aforementioned problems.

SUMMARY OF THE INVENTION

The main objective of the present invention is to provide an assembleable artificial bone plate and artificial bone plate units that save material and take less time to manufacture.

An artificial bone plate unit of a first configuration comprises a plate body, multiple connecting pins and multiple connecting holes. The plate body has two main surfaces and a peripheral surface. The peripheral surface is connected between the two main surfaces. The connecting pins are formed on the plate body and arranged along the peripheral surface on the plate body. The connecting holes are formed in the plate body and arranged along the peripheral surface on the plate body. The connecting holes correspond in shape to the connecting pins. Multiple drug cavities are formed in the artificial bone plate unit. Multiple drug-releasing openings are formed on the artificial bone plate unit, and each of the drug-releasing openings is connected to a respective one of the drug cavities.

The assembleable artificial bone plate is bendable and comprises multiple aforementioned artificial bone plate units. The artificial bone plate units are connected using the connecting pins and the connecting holes.

An artificial bone plate unit of a second configuration comprises a plate body, multiple connecting pins and multiple connecting holes. The plate body has two main surfaces and a peripheral surface. The peripheral surface is connected between the two main surfaces. The connecting pins are formed on the plate body and arranged along the peripheral surface on the plate body. Multiple drug cavities are formed in the artificial bone plate unit. Multiple drug-releasing openings are formed on the artificial bone plate unit, and each of the drug-releasing openings is connected to a respective one of the drug cavities.

An artificial bone plate unit of a third configuration comprises a plate body, multiple connecting pins and multiple connecting holes. The plate body has two main surfaces and a peripheral surface. The peripheral surface is connected between the two main surfaces. The connecting holes are formed in the plate body and arranged along the peripheral surface on the plate body. Multiple drug cavities are formed in the artificial bone plate unit. Multiple drug-releasing openings are formed on the artificial bone plate unit, and each of the drug-releasing openings is connected to a respective one of the drug cavities.

By designing the artificial bone plate units each having the connecting pins and the connecting holes formed on/in the plate body and arranged along the peripheral surface, the artificial bone plate units can be connected with each other using the connecting pins and the connecting holes located in the edge to form a larger piece of an assembleable artificial bone plate. An artificial bone plate for the patient is produced by connecting multiple said artificial bone plate units of the present invention to form a larger piece of the assembleable artificial bone plate, and then bend the assembleable artificial bone plate to make its shape correspond to a shape of a defect area of a skull. In this case, a waste of expensive medical grade material due to machining is prevented, and also the time it takes to produce the artificial bone plate is shorter.

Moreover, with the drug cavities and the drug-releasing openings, the bone plate unit is capable of facilitating wound healing by slowly releasing drugs after a surgery. To be precise, the drugs can be filled in the drug cavities before the surgery, and then the drugs will be slowly released through the drug-releasing openings after the bone plate unit is placed inside a human body.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
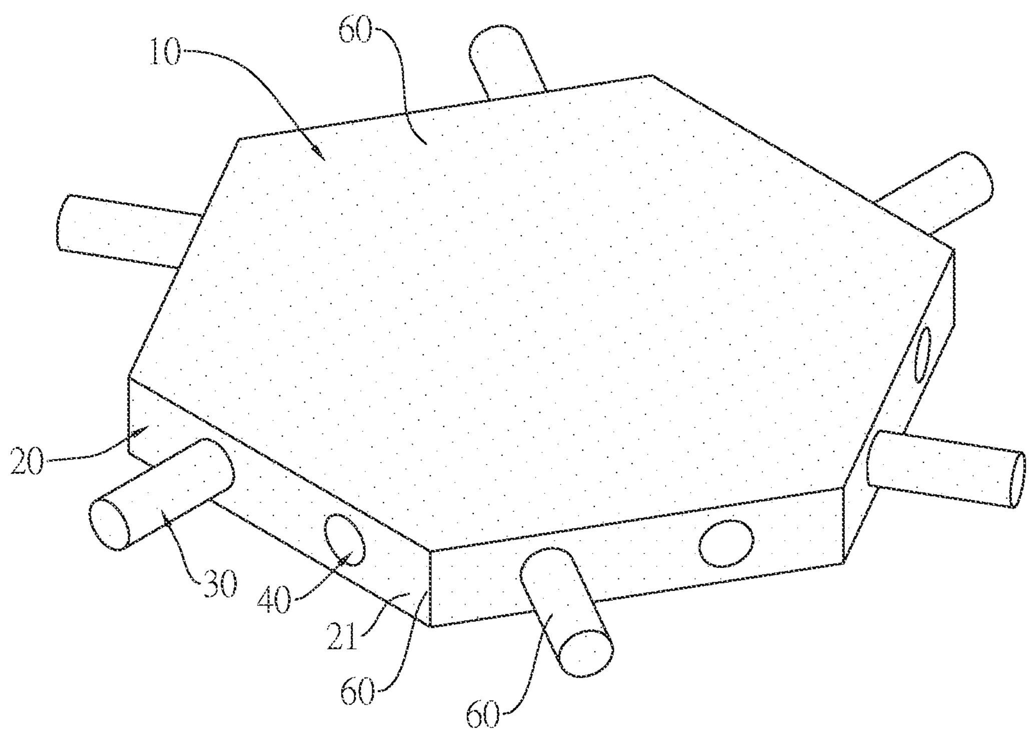
FIG. 1 is a perspective view of a first embodiment of an artificial bone plate unit in accordance with the present invention.
Figure 2:
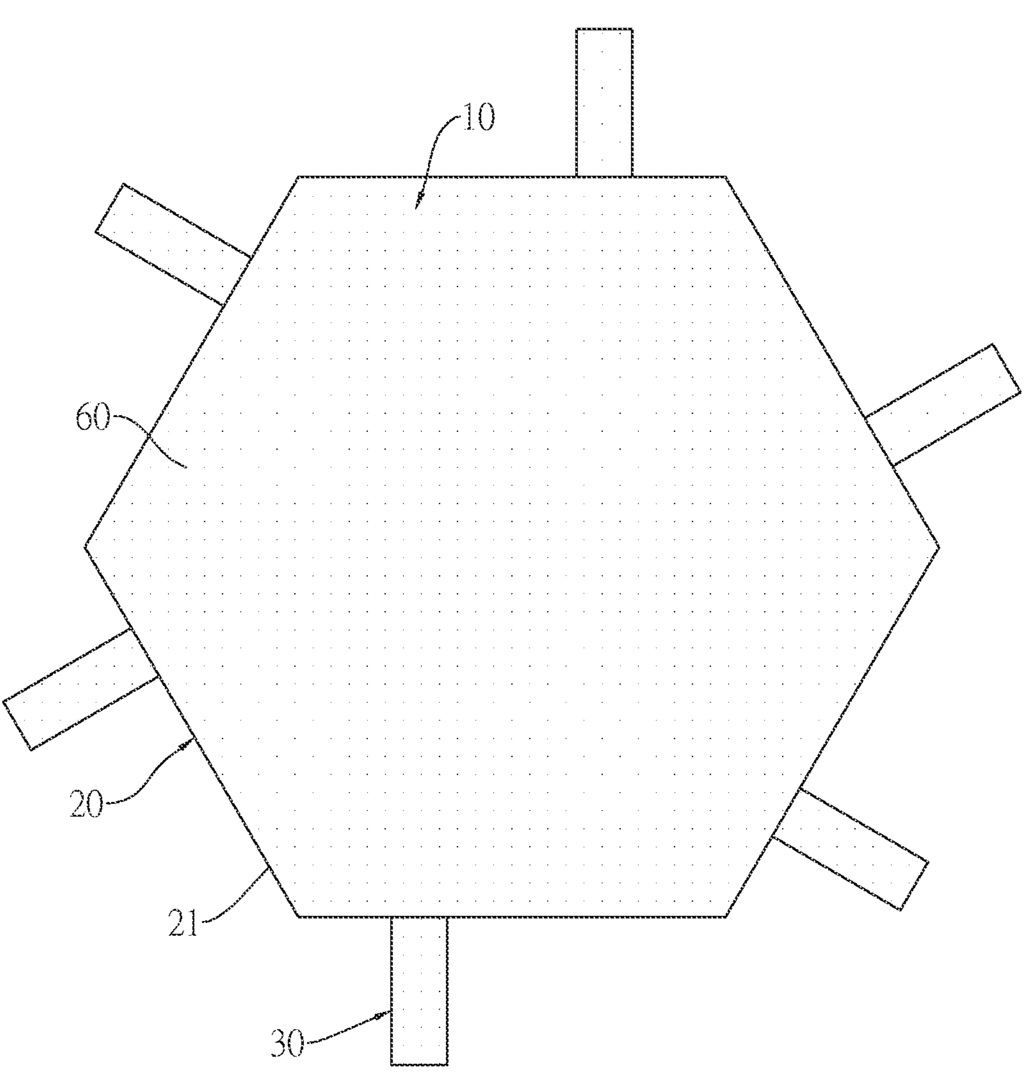
FIG. 2 is a top view of the artificial bone plate unit in FIG. 1.
Figure 3:
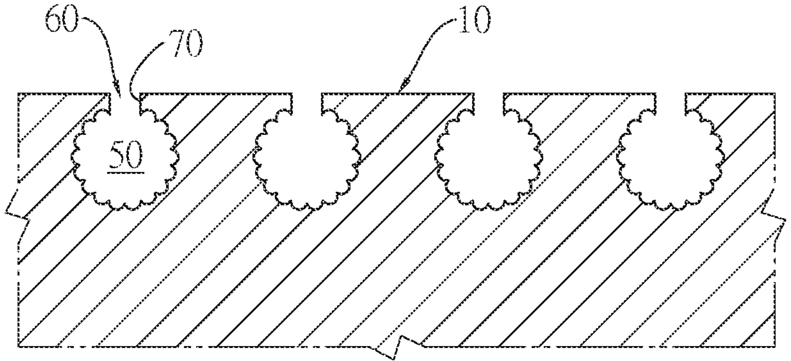
FIG. 3 is an enlarged longitudinal section view of the artificial bone plate unit in FIG. 1.

With reference to FIGS. 1 to 3, an artificial bone plate unit in accordance with the present invention comprises a plate body, multiple connecting pins 30 multiple connecting holes 40, multiple drug cavities 50, and multiple drug-releasing openings 60. The plate body has two main surfaces 10, a peripheral surface 20, multiple connecting pins 30 and multiple connecting holes 40. The peripheral surface 20 is connected between the two main surfaces 10.

The connecting pins 30 and the connecting holes 40 are formed on the plate body and arranged along the peripheral surface 20 on the plate body. The connecting holes 40 correspond in shape to the connecting pins 30, which means two artificial bone plate units in accordance with the present invention can be assembled together by engaging one of the connecting pins 30 of one plate unit with one of the connecting holes 40 of the other plate unit.

The drug cavities 50 (as shown in FIG. 3) are formed in the artificial bone plate unit. The drug-releasing openings 60 are formed on the artificial bone plate unit, and each of the drug-releasing openings 60 is connected to a respective one of the drug cavities 50 such that drugs can be prefilled in the drug cavities 50 before surgery, and then drugs in the drug cavities 50 will be slowly released after the artificial bone plate unit is placed inside a human body.

In the preferred embodiment, the drug cavities 50 are formed in the plate body and the connecting pins 30; the drug-releasing openings 60 are formed on the two main surfaces 10, the peripheral surface 20, and all outer surfaces of the connecting pins 30; that is, the drug-releasing openings 60 and the drug cavities 50 are disposed on all outer surfaces of the artificial bone plate unit. In another preferred embodiment, the drug-releasing openings 60 and the drug cavities 50 are disposed only on the plate body. The drug cavities 50 and the drug-releasing openings 60 are preferably formed together by etching.

Moreover, the artificial bone plate unit preferably has multiple drug-releasing channels 70. Each of the drug-releasing channels 70 connects a respective one of the drug-releasing openings 60 and a respective one of the drug cavities 50; that is, the drug-releasing openings 60 and the drug cavities 50 are connected via the drug-releasing channels 70. In another preferred embodiment, the drug-releasing channels 70 are omitted, and the drug-releasing openings 60 and the drug cavities 50 are directly connected.

With reference to FIGS. 3 to 8, detailed dimensions and shapes of the drug cavities 50 are further explained using cross section and longitudinal section of the drug cavities 50. A normal direction of the cross section of each of the drug cavities 50 is parallel to an opening direction of the corresponding drug-releasing opening 60, while a normal direction of the longitudinal section of each of the drug cavities is perpendicular to an opening direction of the corresponding drug-releasing opening 60.

Figure 4:
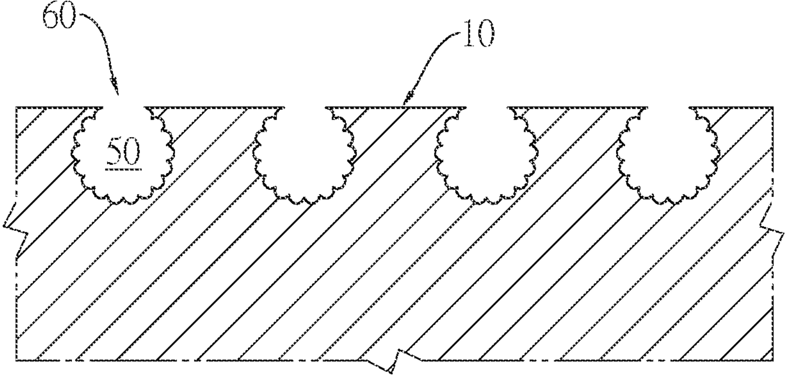
FIGS. 4 to 8 are enlarged longitudinal section views of other artificial bone plate units in accordance with the present invention.
Figure 5:
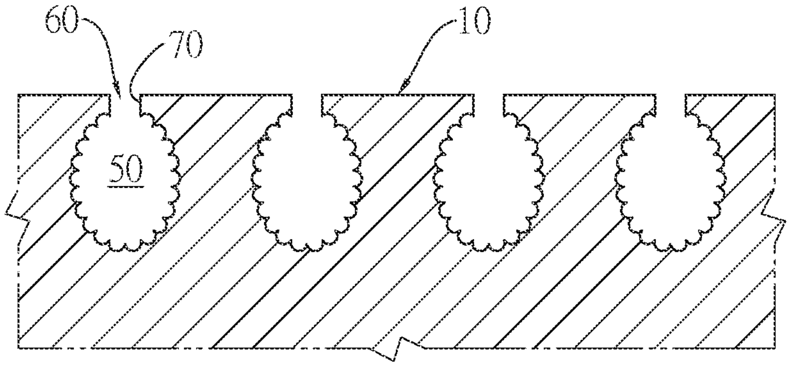
Figure 6:
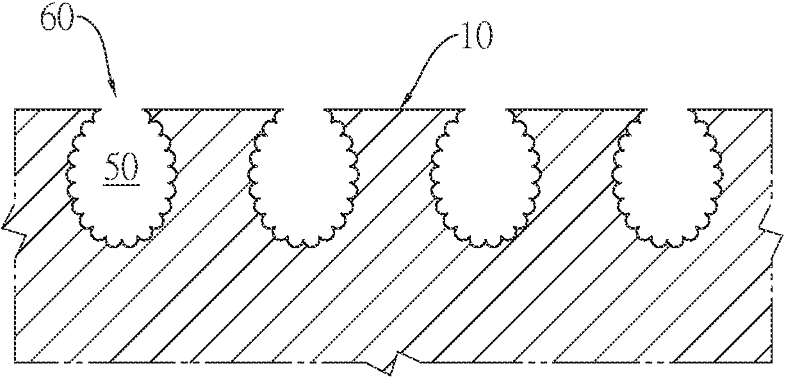

In the preferred embodiment, a maximum area of the cross section of each of the drug cavities 50 is greater than an area of a corresponding one of the drug-releasing openings 60. As a result, drug in the drug cavity 50 will be released slowly for a longer period of time due to the relatively small drug-releasing opening 60. Shape of a longitudinal section of each of the drug cavities 50 is a circle (as shown in FIGS. 3 and 4), an ellipse (as shown in FIGS. 5 and 6), or an ovoid.

Figure 7:
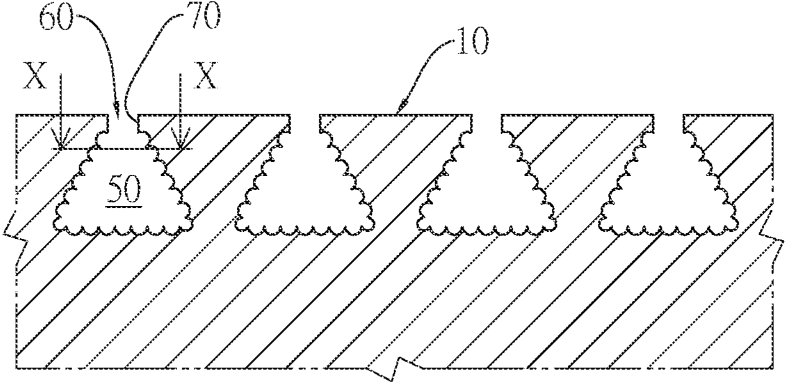
Figure 8:
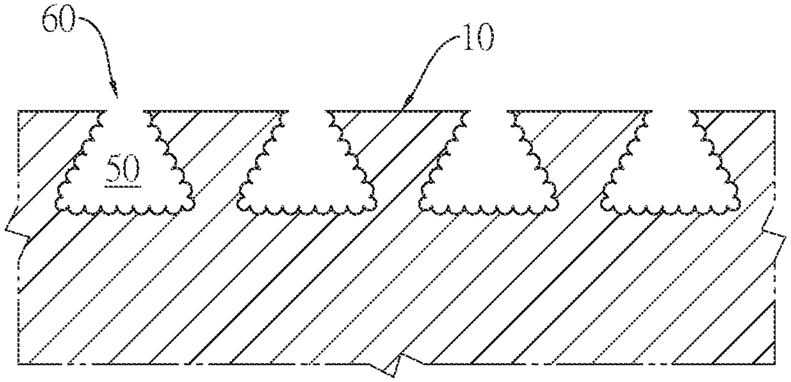

With reference to FIGS. 7 and 8, in another preferred embodiment, the area of the cross section of each of the drug cavities 50 increases as a cutting plane X-X of the cross section moves away from the corresponding drug-releasing opening 60. In this particular embodiment, the shape of the longitudinal section of each of the drug cavities 50 is preferably a triangle.

Figure 15:
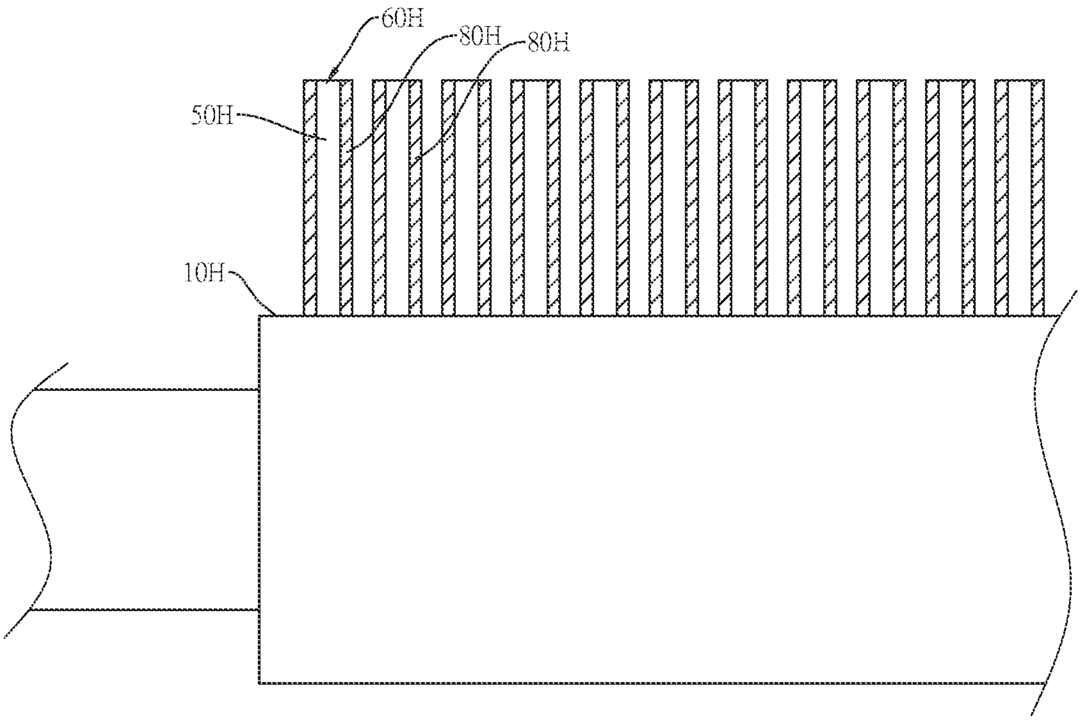
FIG. 15 is an enlarged longitudinal section view of the artificial bone plate unit in FIG. 14.

With reference to FIGS. 1 and 2, the connecting pins 30 and the connecting holes 40 are preferably formed on the peripheral surface 20 of the plate body, and therefore when multiple said artificial bone plate units are assembled together to form an assembleable artificial bone plate, a surface of the assembleable artificial bone plate is substantially smooth as edges of the plate bodies do not protrude therefrom. However, positions of the connecting pins 30 and the connecting holes 40 are not limited by the abovementioned, as long as the connecting pins 30 and the connecting holes 40 are arranged along the peripheral surface 20 on/in the plate body, which means the connecting pins and the connecting holes 40 only have to surround or be arranged along the peripheral surface 20, and do not have to be located on the peripheral surface 20. To be precise, the connecting pins 30 and the connecting holes 40 can be formed on the peripheral surface 20 as shown in FIG. 1, or the connecting pins 30F and the connecting holes 40F can be formed on the main surface 10F and located adjacent to an edge of the peripheral face 20F as shown in FIG. 15.

The plate body in a preferred embodiment is a six-sided polygon, and to be precise, the plate body is a regular hexagon, such that the six connecting faces 21 are formed on the peripheral surface 20. A number of the connecting pins 30 is six, and each of the six connecting pins 30 is formed on a respective one of the six connecting faces. A number of the connecting holes 40 is six, and each of the six connecting holes 40 is formed in a respective one of the six connecting faces 21.

In another preferred embodiment, the plate body can be an N-sided polygon other than hexagon, where N is an integer greater than 2. When the plate body is the N-sided polygon other than hexagon, a number of the connecting faces 21, the number of the connecting pins 30, and the number of the connecting holes 40 are N. Each of the N connecting pins 30 is formed on a respective one of the N connecting faces 21, and each of the N connecting holes 40 is formed in a respective one of the N connecting faces 21. In other words, each side of the N-sided polygonal plate body has a connecting pin 30 and a connecting hole 40.

Figure 9:
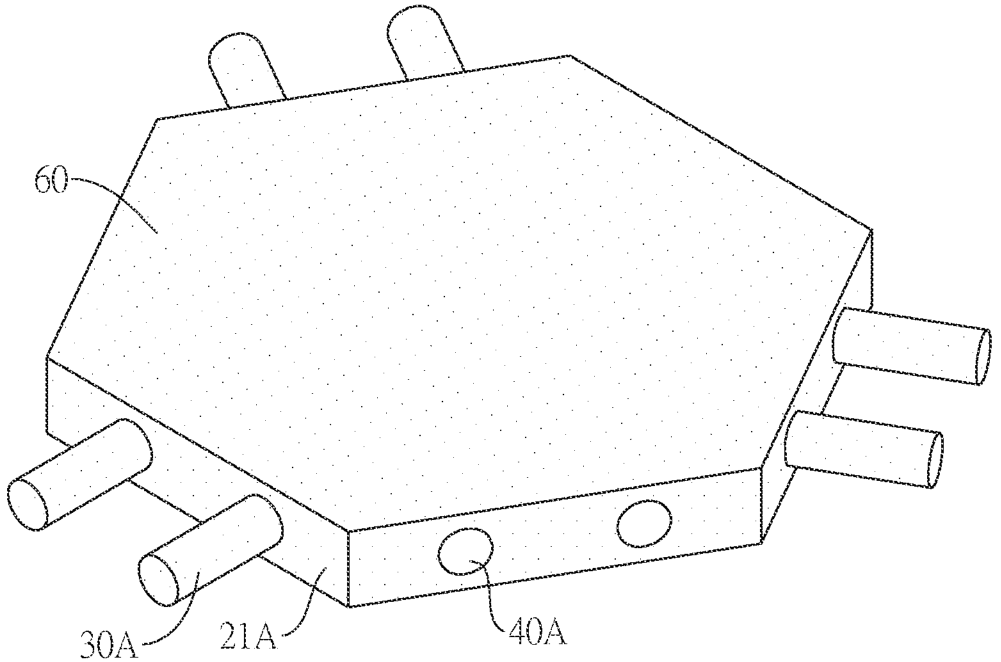
FIG. 9 is a perspective view of a second embodiment of an artificial bone plate unit in accordance with the present invention.

Moreover, a number of the connecting pin 30 on each connecting face 21 and a number of the connecting hole 40 on each connecting face 21 are not limited to one. For example, in a second embodiment in accordance with the present invention (as shown in FIG. 9), some connecting faces 21A have two connecting pins 30A but no connecting hole 40A, while other connecting faces 21A have two connecting holes 40A but no connecting pins 30A.

Figure 11:
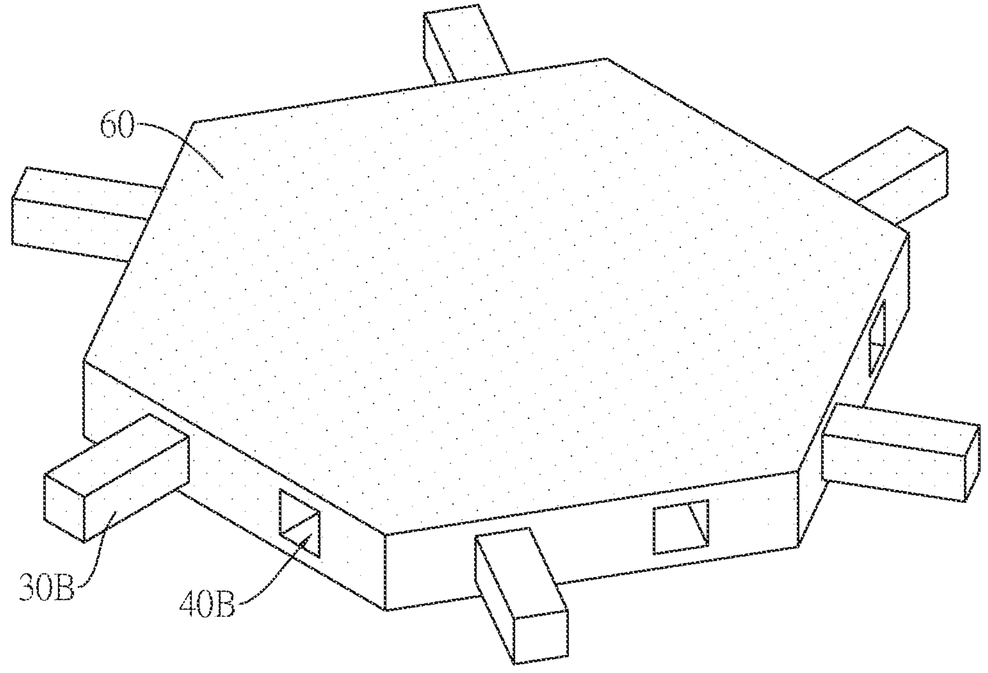
FIG. 11 is a perspective view of a fourth embodiment of an artificial bone plate unit in accordance with the present invention.
Figure 12:
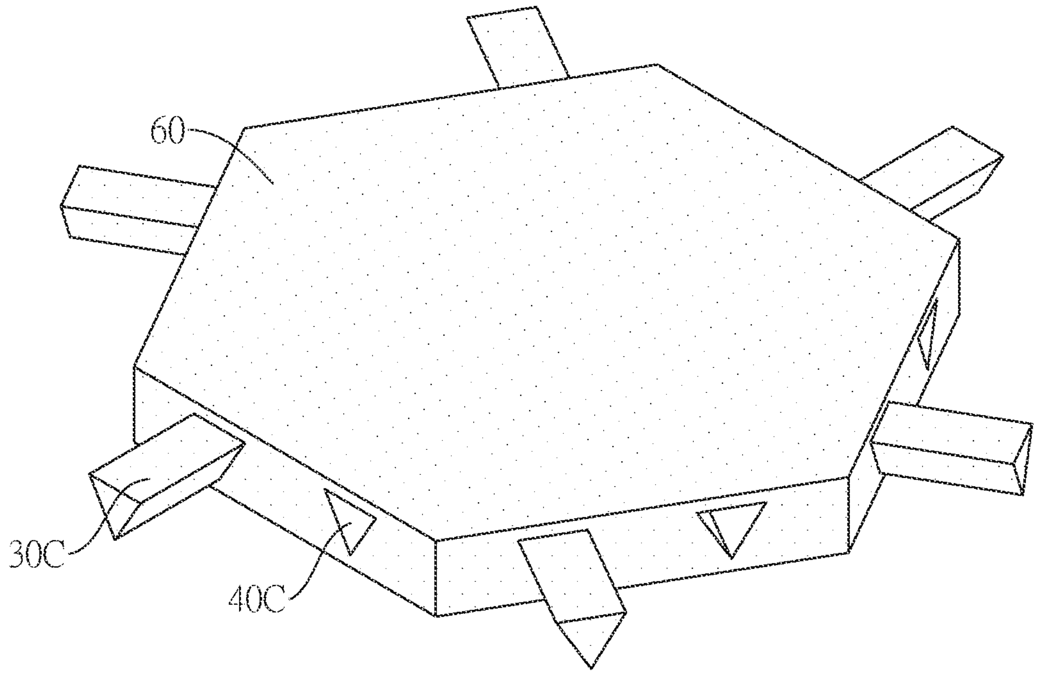
FIG. 12 is a perspective view of a fifth embodiment of an artificial bone plate unit in accordance with the present invention.
Figure 13:
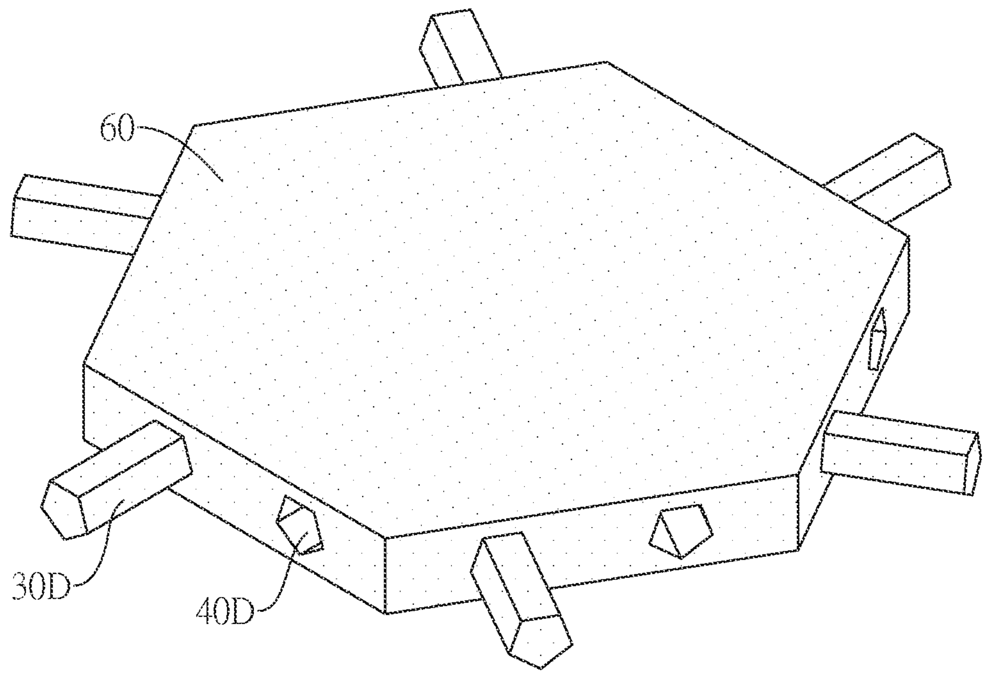
FIG. 13 is a perspective view of a sixth embodiment of an artificial bone plate unit in accordance with the present invention.

A shape of the connecting pin 30 is cylindrical, while the connecting hole 40 is a round recess, which corresponds to the shape of the connecting pin 30. However, the shapes of the connecting pin 30 and connecting hole 40 are not limited to the abovementioned, and can be of other shapes depending on the application. For example, the connecting pin 30B can be a quadrilateral prism as shown in FIG. 11, while the connecting hole 40B is a square hole; or the connecting pin 30C can be a triangular prism as shown in FIG. 12, while the connecting hole 40C is a triangular hole; or the connecting pin 30D can be a pentagonal prism as shown in FIG. 13, while the connecting hole 40D is a pentagonal hole.

Figure 10:
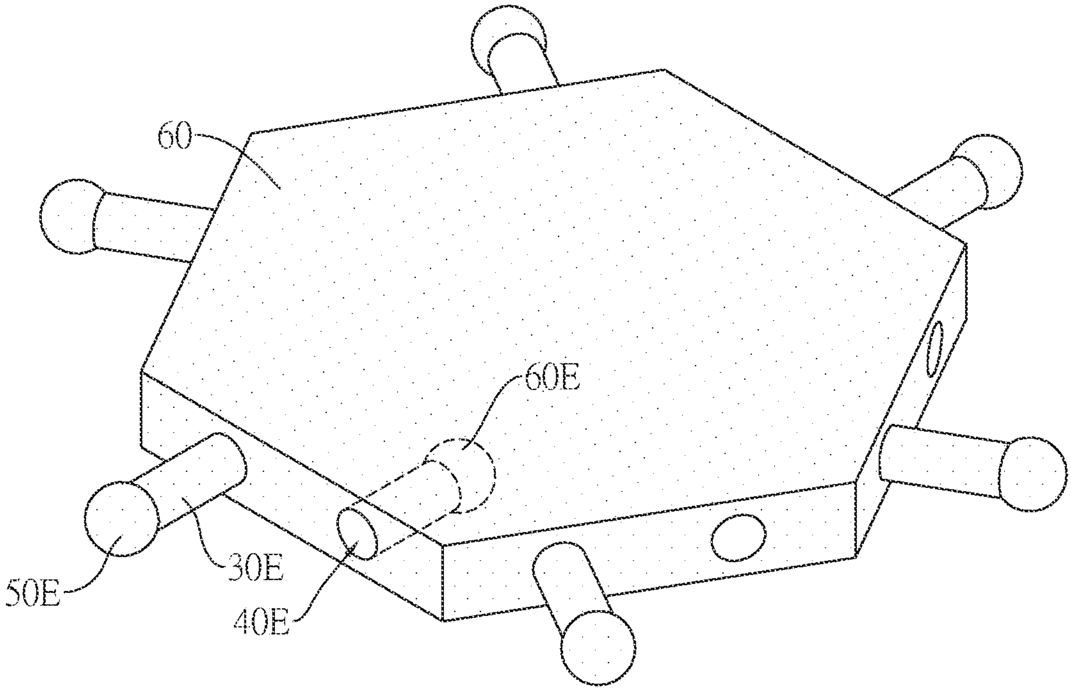
FIG. 10 is a perspective view of a third embodiment of an artificial bone plate unit in accordance with the present invention.

In another preferred embodiment, a round connecting ball 50E is connected to the tip of the connecting pin 30E (as shown in FIG. 10), and a diameter of the connecting ball 50E is greater than a diameter of the connecting pin 30E. A round connecting cavity 60E is formed in a bottom of the round connecting hole 40E, and a diameter of the connecting cavity 60E corresponds to the diameter of the connecting ball 50E. In this case, when connecting two of the artificial bone plate units, the connecting ball 50E can be pressed through the connecting hole 40E and forcing a diameter of the connecting hole 40E to expand elastically, and finally the connecting ball 50E is pressed through the connecting hole 40E and engages with the connecting cavity 60E. A strength of the connection between said two artificial bone plate units is further enhanced to prevent separation when the two artificial bone plate units are pulled in opposite directions respectively.

Figure 14:
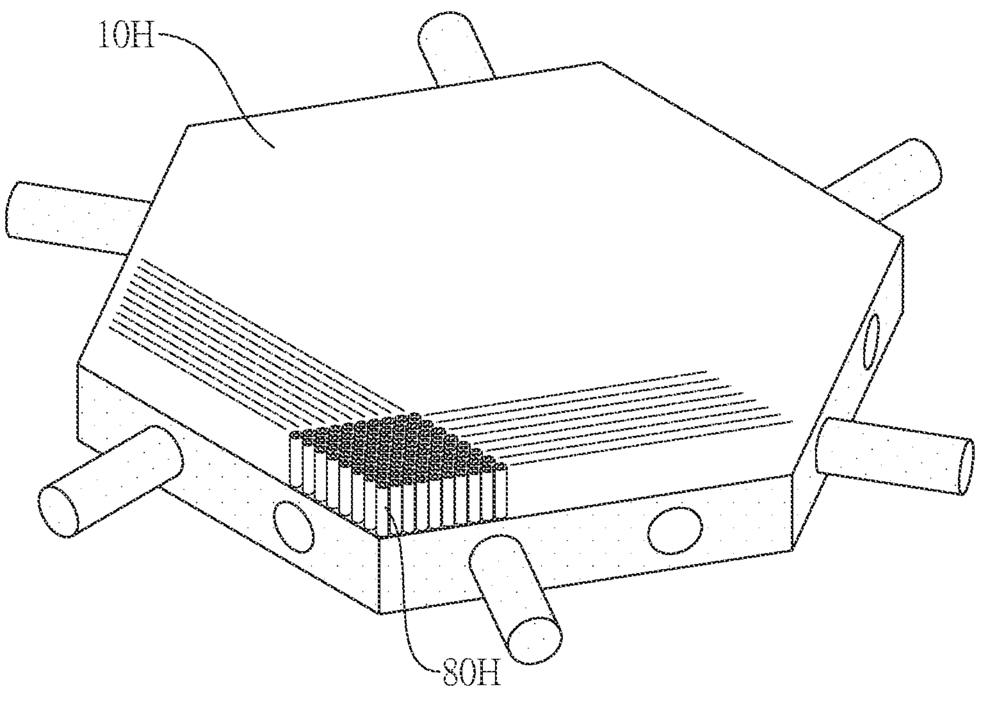
FIG. 14 is a perspective view of a seventh embodiment of an artificial bone plate unit in accordance with the present invention.

With reference to FIGS. 14 and 15, a seventh embodiment of an artificial bone plate unit in accordance with the present invention is substantially similar to the first embodiment, but the difference is that multiple drug pins 80H are formed on one of the main surfaces 10H of the plate body. Each of the drug pins 80H has one of the drug cavities 50H formed in the drug pin and one of the rug-releasing openings 60H formed on a distal end of the drug pin 80H and connected to the corresponding drug cavity 50H. The drug pins 80H are preferably micro tubes formed by special chemical procedures, and are preferably intensely arranged the main surface 10H.

Figure 16:
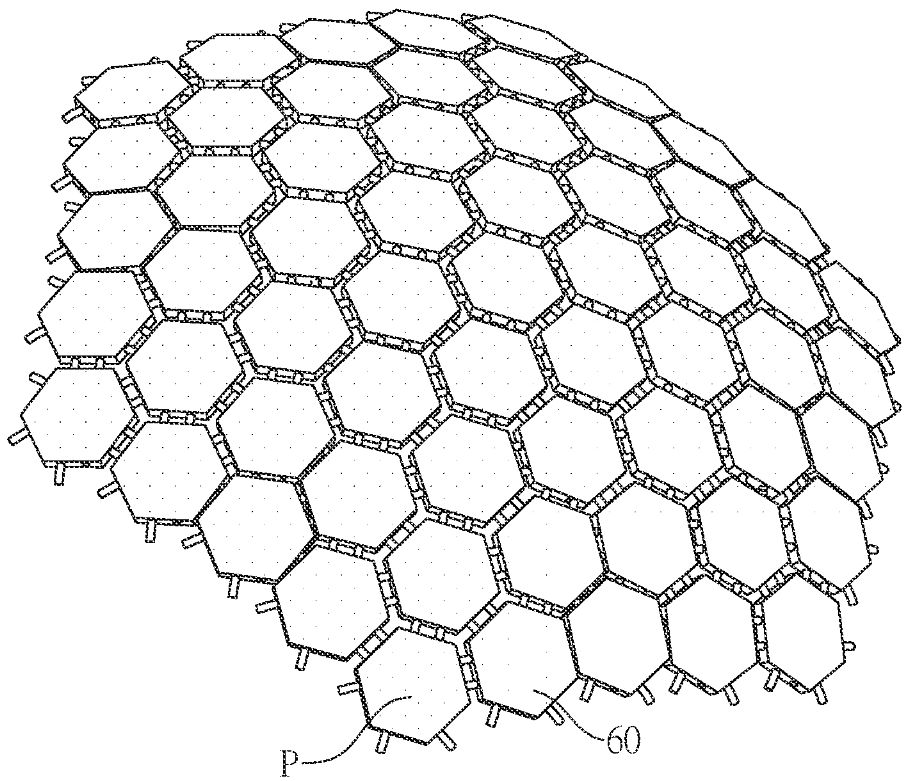
FIG. 16 is a perspective view of a first embodiment of an assembleable artificial bone plate in accordance with the present invention.

With reference to FIG. 16, an assembleable artificial bone plate in accordance with the present invention is bendable. The assembleable artificial bone plate comprises multiple said artificial bone plate units P. The artificial bone plate units P are connected to each other. Among any two of the artificial bone plate units P that are connected to each other, at least one of the connecting pins 30 on one of said two artificial bone plate units P is mounted inside the at least one of the connecting holes 40 in the other one of said two artificial bone plate units P. In a preferred embodiment, the assembleable artificial bone plate is formed by having the artificial bone plate units P connected to each other through the connecting pins 30 and the connecting holes 40 located on the peripheral surface 20, and the artificial bone plate units P are in accordance with the first embodiment of the present invention, but an assembleable artificial bone plate can also be formed by the artificial bone plate units of another embodiment.

Figure 17:
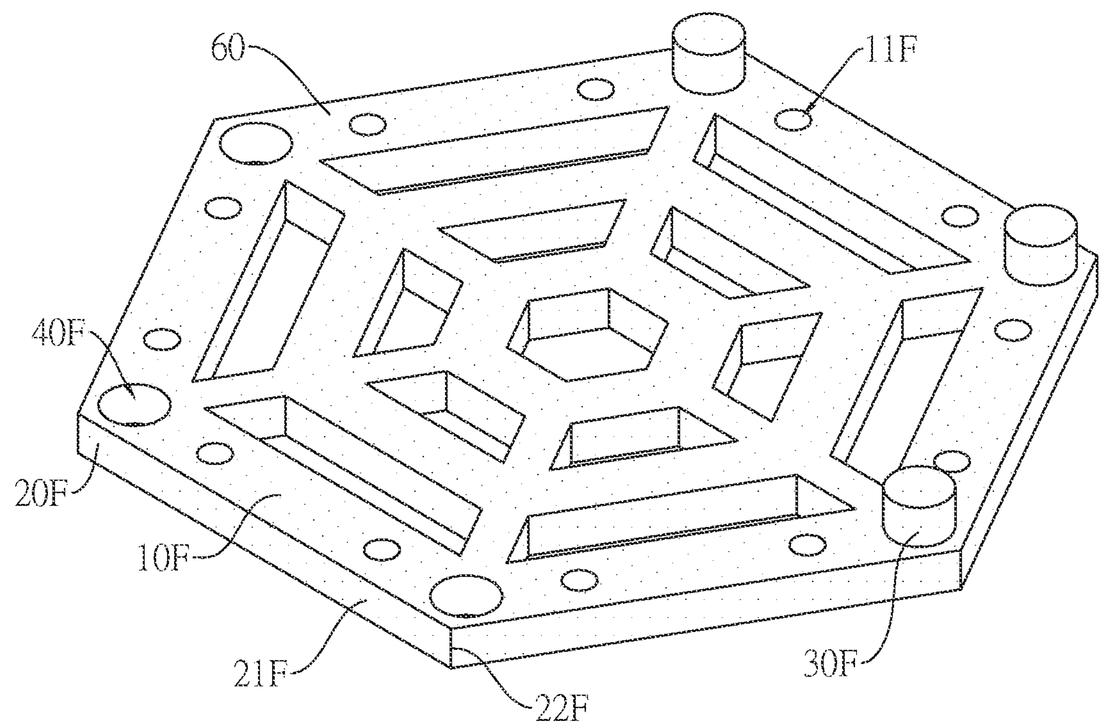
FIG. 17 is a perspective view of an eighth embodiment of an artificial bone plate unit in accordance with the present invention.
Figure 18:
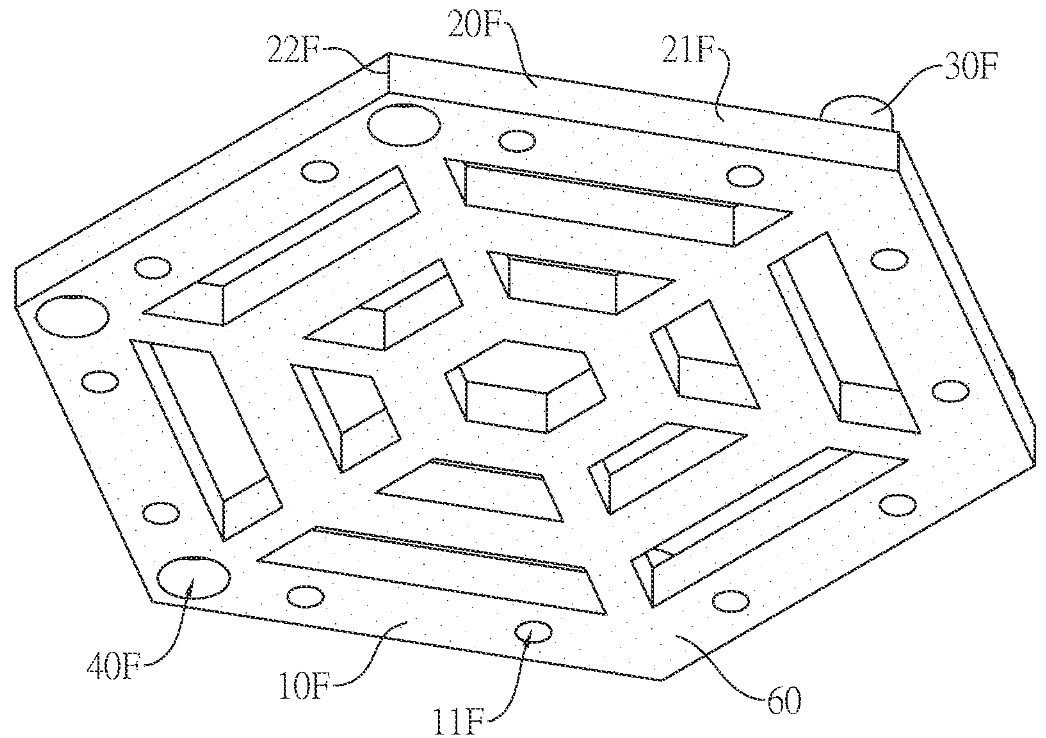
FIG. 18 is another perspective view of the artificial bone plate unit in FIG. 17.

With reference to FIGS. 17 and 18, an eighth embodiment of the artificial bone plate unit in accordance with the present invention is substantially similar to the first embodiment mentioned above, but the connecting pins 30F and the connecting holes 40F are formed in different positions.

The connecting pins 30F are formed on one of the two main surfaces 10F. The connecting holes 40F are formed through the two main surfaces 10F of the artificial bone plate unit. In a preferred embodiment, multiple screw holes 11F are formed through the two main surfaces 10F, and the screw holes 11F are arranged along the peripheral face 20F of the plate body. However, positions of the screw holes 11F are not limited by abovementioned positions, and the plate body may optionally have no screw holes 11F.

In a preferred embodiment, the plate body is polygonal, such that multiple corner portions 22F are formed on the peripheral surface 20F. Each of the connecting pins 30F is disposed adjacent to one of the corner portions 22F, and each of the connecting holes 40F is disposed adjacent to one of the corner portions 22F. To be precise, the plate body is a six-sided polygon, and the corner portions 22F are located adjacent to the corner positions of the polygonal plate body. However, positions of the connecting pins 30F and the connecting holes 40F are not limited by abovementioned positions. For example, the connecting pins 30F and the connecting holes 40F can be located in the middle of two of the adjacent corner portions 22F.

In a preferred embodiment, the plate body is an N-sided polygon, such that the peripheral surface 20F comprises N connecting faces 21F. A sum of a number of the connecting pins 30F and a number of the connecting holes 40F is N. To be precise, N is six, and the plate body is hexagonal, such that the peripheral surface 20F comprises N connecting faces 21F. Three connecting pins 30F and three connecting holes 40F are formed on the plate body, making the sum of the number of the connecting pins 30F and the number of the connecting holes 40F be six, through which a polygonal plate body can be securely connected to an adjacent polygonal plate body. However, the sum of the number of the connecting pins 30F and the number of the connecting holes 40F is not limited by the abovementioned. For example, the sum of the number of the connecting pins 30F and the number of the connecting holes 40F in the polygonal plate body can be twelve.

Figure 19:
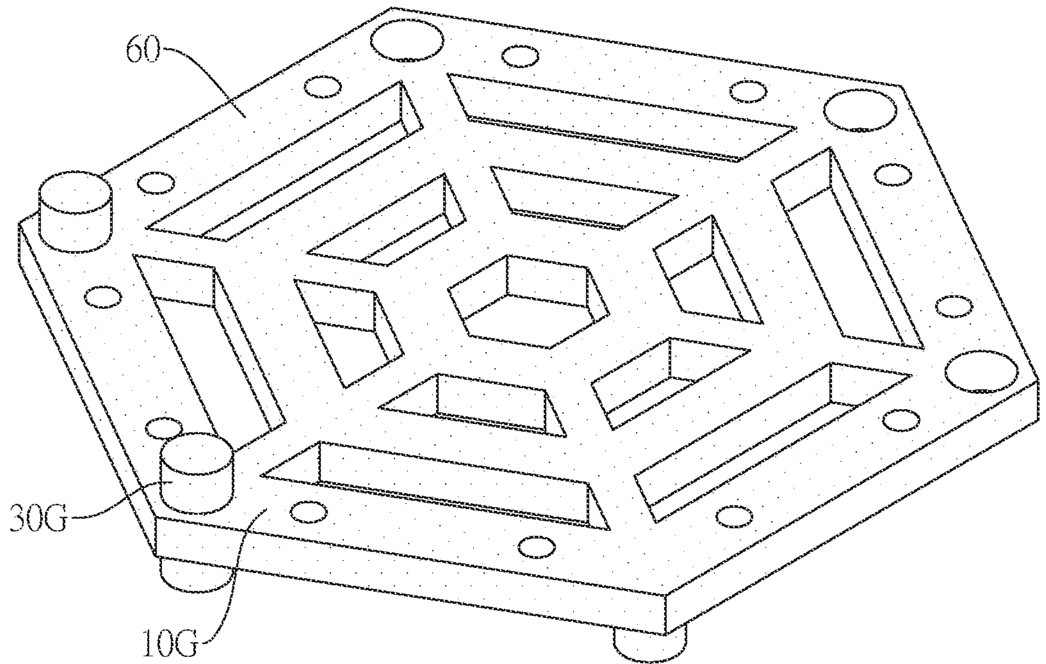
FIG. 19 is a perspective view of a ninth embodiment of an artificial bone plate unit in accordance with the present invention.
Figure 20:
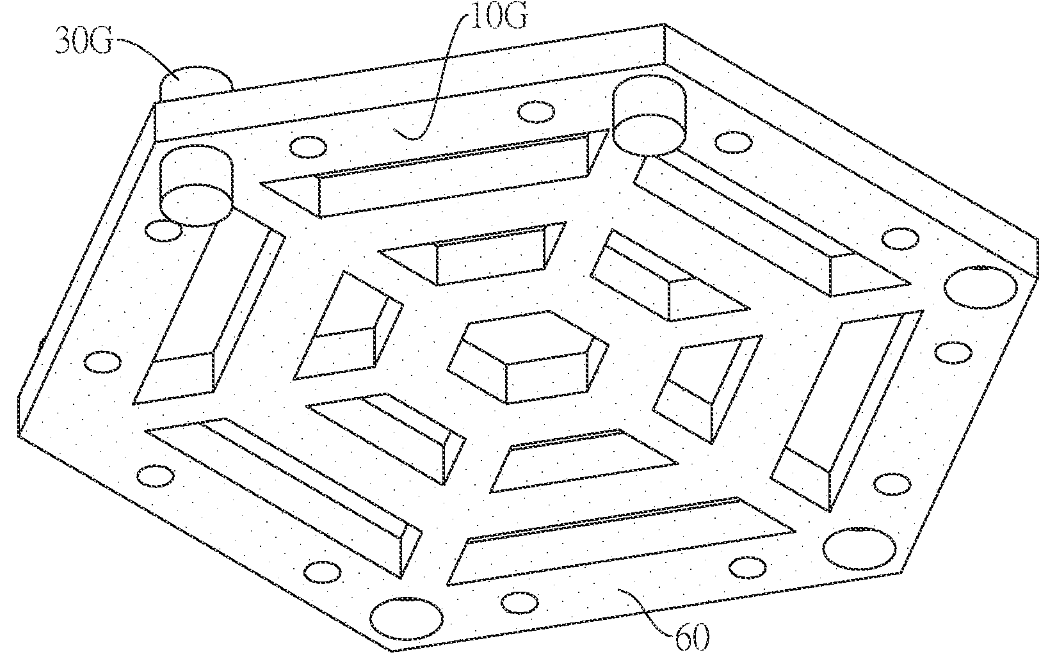
FIG. 20 is another perspective view of the artificial bone plate unit in FIG. 19.

With reference to FIGS. 19 and 20, an ninth embodiment of the artificial bone plate unit is substantially similar to the eighth embodiment mentioned above, but the connecting pins 30G are formed on a respective one of the two main surfaces 10G. The connecting pins 30G can be located symmetrically on the two main surfaces 10G, which means all connecting pins 30G are formed through the plate body; the connecting pins 30G can also be located asymmetrically, which means some of the connecting pins 30G are formed through the plate body, while the remaining connecting pins 30G are only formed on either side of the plate body.

A distance between the two main surfaces 10F is defined as a thickness of the plate body. The thickness of the plate body in the aforementioned eighth and ninth embodiments of the artificial bone plate unit is less than 1 mm, but the thickness of the plate body in the embodiment wherein the connecting pins 30F and the connecting holes 40F are formed on the main surface 10F is not limited by abovementioned as long as the plate body can be deformed when bended to satisfy the need of a surgical repair.

In all the abovementioned embodiments of the artificial bone plate unit, the artificial bone plate unit can be made of a material with good biocompatibility and mechanical strength, such as titanium, Ti-6Al-4V, 316L stainless steel or polyether ether ketone (PEEK). The artificial bone plate unit can also be made of aluminum for reduced weight and cost. Moreover, all the abovementioned embodiments of the artificial bone plate unit comprise the drug cavities 50 and the drug-releasing openings 60 for releasing the drugs.

Figure 21:
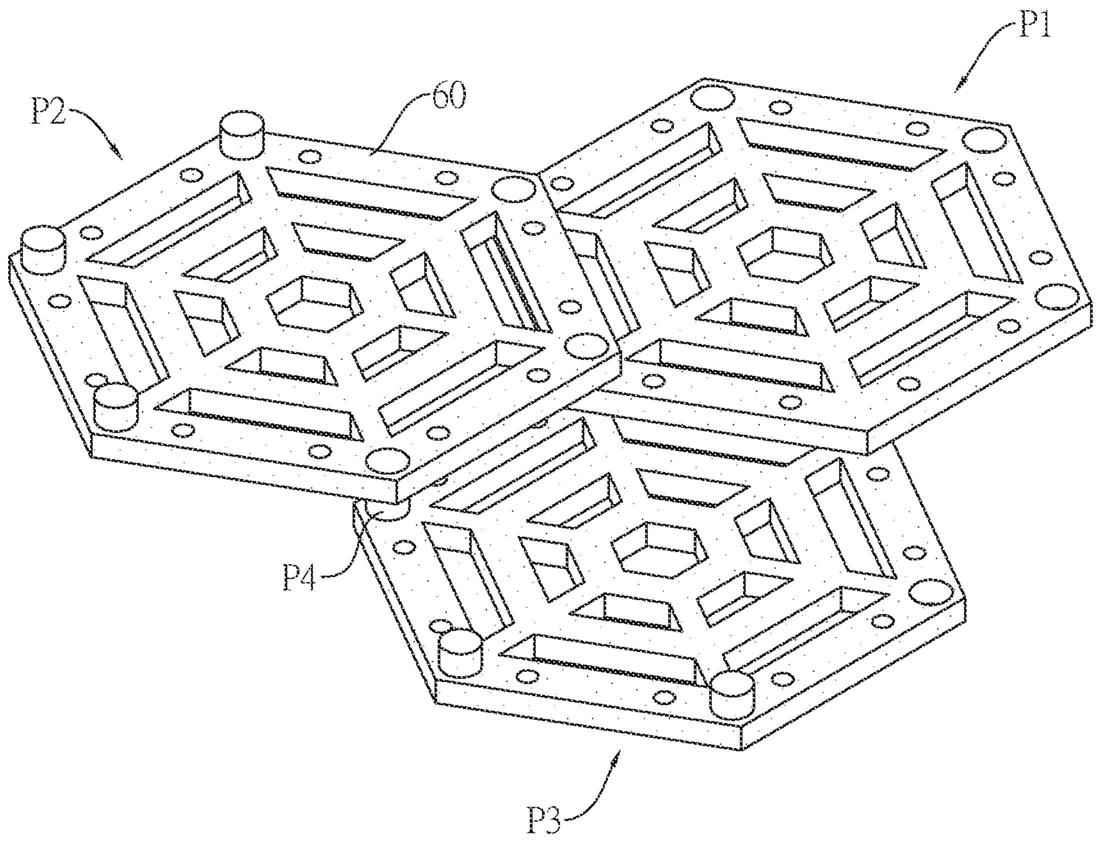
FIG. 21 is a perspective view of a second embodiment of an assembleable artificial bone plate in accordance with the present invention.

With reference to FIG. 21, a second embodiment of the assembleable artificial bone plate is substantially similar to the first embodiment mentioned above, but the difference is that the connecting pins and the connecting holes are formed on the main surfaces of the artificial bone plate units, and therefore the edges of the artificial bone plate units are overlapped. Three different embodiments of the artificial bone plate units are present in said assembleable artificial bone plate: the artificial bone plate unit P1 corresponds to the ninth embodiment as shown in FIG. 19; the artificial bone plate unit P2 corresponds to the eighth embodiment as shown in FIG. 17; the artificial bone plate unit P3 is substantially similar to the eighth embodiment mentioned above, but a length of one of the connecting pins P4 is longer than the other connecting pins in order to connect the artificial bone plate unit P2.

To use the present invention, first connect several artificial bone plate units together to form a larger piece of the assembleable artificial bone plate, and then bend the assembleable artificial bone plate to make the shape of the assembleable artificial bone plate correspond to the shape of a defect area of a skull.

When the assembleable artificial bone plate is of the second embodiment (as shown FIG. 21), the edge of the assembleable artificial bone plate overlaps with the surface of the skull, and screws can be used to fasten the assembleable artificial bone plate to the skull through the screw holes on the artificial bone plate units.

When the assembleable artificial bone plate is of the first embodiment (as shown FIG. 16), the assembleable artificial bone plate can be embedded and fixed to the defect area of the skull after trimming the edge of the assembleable artificial bone plate properly.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An artificial bone plate unit comprising:
- a plate body formed unitarily and having
  - two main surfaces;
  - a peripheral surface connected between the two main surfaces;
- multiple connecting pins formed on the plate body and arranged along the peripheral surface on the plate body;
- multiple connecting holes formed in the plate body and arranged along the peripheral surface in the plate body; the connecting holes corresponding in shape to the connecting pins;
- multiple drug cavities formed in the artificial bone plate unit;
- multiple drug-releasing openings formed on the artificial bone plate unit; each of the drug-releasing openings connected to a respective one of the drug cavities;
- multiple drug-releasing channels; each of the drug-releasing channels connecting a respective one of the drug-releasing openings and a respective one of the drug cavities, such that a drug disposed within each of the multiple drug cavities is released directly through the respective one of the drug-releasing channels and the respective one of the drug-releasing openings; and
- wherein a maximum area of a cross section of each of the drug cavities is greater than an area of a cross section of the respective one of the drug-releasing channels.

2. The artificial bone plate unit as claimed in claim 1, wherein:
- the maximum area of the cross section of each of the drug cavities is greater than an area of a corresponding one of the drug-releasing openings; and
- a normal direction of the cross section of each of the drug cavities is parallel to an opening direction of the corresponding drug-releasing opening.

3. The artificial bone plate unit as claimed in claim 1, wherein:
- a shape of a longitudinal section of each of the drug cavities is a circle, an ellipse, an ovoid, or a triangle; and
- a normal direction of the longitudinal section of each of the drug cavities is perpendicular to an opening direction of the corresponding drug-releasing opening.

4. The artificial bone plate unit as claimed in claim 1, wherein:
- an area of the cross section of each of the drug cavities increases as a cutting plane of the cross section moves away from the corresponding drug-releasing opening; and
- a normal direction of the cross section of each of the drug cavities is parallel to an opening direction of the corresponding drug-releasing opening.

5. The artificial bone plate unit as claimed in claim 1, wherein the connecting pins and the connecting holes are located on the peripheral surface of the plate body.

6. The artificial bone plate unit as claimed in claim 5, wherein
- the plate body is an N-sided polygon such that the peripheral surface comprises N connecting faces;
- a number of the connecting pins is N, and each of the connecting pins is formed on a respective one of the N connecting faces;
- a number of the connecting holes is N, and each of the connecting holes is formed in a respective one of the N connecting faces;
- wherein N is an integer greater than two.

7. The artificial bone plate unit as claimed in claim 1, wherein
- the connecting pins are formed on one of the two main surfaces;
- the connecting holes are formed through the two main surfaces.

8. The artificial bone plate unit as claimed in claim 1, wherein
- the connecting pins are formed on the two main surfaces;
- the connecting holes are formed through the two main surfaces.

9. The artificial bone plate unit as claimed in claim 7, wherein multiple screw holes are formed through the two main surfaces and are arranged along the peripheral surface.

10. The artificial bone plate unit as claimed in claim 1, wherein the plate body is polygonal, such that the peripheral surface comprises multiple corner portions; each of the connecting pins is disposed adjacent to one of the corner portions; each of the connecting holes is disposed adjacent to one of the corner portions.

11. The artificial bone plate unit as claimed in claim 1, wherein the plate body is an N-sided polygon, such that the peripheral surface comprises N connecting faces; a sum of a number of the connecting pins and a number of the connecting holes is N; N is an integer greater than 2.

12. The artificial bone plate unit as claimed in claim 7, wherein a thickness of the plate body is less than 1 mm.

13. The artificial bone plate unit as claimed in claim 1, wherein the artificial bone plate unit is made of titanium, Ti-6Al-4V, 316L stainless steel, polyether ether ketone, or aluminum.

14. The artificial bone plate unit as claimed in claim 1, wherein multiple drug pins formed on one of the main surfaces of the plate body; each of the drug pins has one of the drug cavities formed in the drug pin;

one of the drug-releasing openings formed on a distal end of the drug pin and connected to the corresponding drug cavity.

15. An assembleable artificial bone plate being bendable and comprising multiple said artificial bone plate units as claimed in claim 1; the artificial bone plate units connected to each other; among any two of the artificial bone plate units that are connected to each other, at least one of the connecting pins on one of said two artificial bone plate units mounted inside a respective one of the connecting holes in the other one of said two artificial bone plate units.

16. An artificial bone plate unit comprising:

a plate body formed unitarily and having two main surfaces;

a peripheral surface connected between the two main surfaces;

multiple connecting pins formed on the plate body and arranged along the peripheral surface on the plate body;

multiple drug cavities formed in the artificial bone plate unit; and multiple drug-releasing openings formed on the artificial bone plate unit; each of the drug-releasing openings connected to a respective one of the drug cavities;

multiple drug-releasing channels; each of the drug-releasing channels connecting a respective one of the drug-releasing openings and a respective one of the drug cavities, such that a drug disposed within each of the multiple drug cavities is released directly through the respective one of the drug-releasing channels and the respective one of the drug-releasing openings; and wherein a maximum area of a cross section of each of the drug cavities is greater than an area of a cross section of the respective one of the drug-releasing channels.

17. An artificial bone plate unit comprising:

a plate body formed unitarily and having two main surfaces;

a peripheral surface connected between the two main surfaces;

multiple connecting pins formed on the plate body and arranged along the peripheral surface on the plate body;

multiple connecting holes formed in the plate body and arranged along the peripheral surface in the plate body; and multiple drug cavities formed in the artificial bone plate unit;

multiple drug-releasing openings formed on the artificial bone plate unit; each of the drug-releasing openings connected to a respective one of the drug cavities;

multiple drug-releasing channels; each of the drug-releasing channels connecting a respective one of the drug-releasing openings and a respective one of the drug cavities, such that a drug disposed within each of the multiple drug cavities is released directly through the respective one of the drug-releasing channels and the respective one of the drug-releasing openings; and wherein a maximum area of a cross section of each of the drug cavities is greater than an area of a cross section of the respective one of the drug-releasing channels.

* * * * *